(12) United States Patent
Boppart et al.

(10) Patent No.: US 11,083,375 B2
(45) Date of Patent: Aug. 10, 2021

(54) HANDHELD DEVICE FOR IDENTIFICATION OF MICROBIOLOGICAL CONSTITUENTS IN THE MIDDLE EAR

(71) Applicant: The Board of Trustees of the University of Illinois, Urbana, IL (US)

(72) Inventors: Stephen A. Boppart, Champaign, IL (US); Ryan L. Shelton, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 438 days.

(21) Appl. No.: 16/012,201

(22) Filed: Jun. 19, 2018

(65) Prior Publication Data
US 2018/0303348 A1    Oct. 25, 2018

Related U.S. Application Data

(62) Division of application No. 14/722,344, filed on May 27, 2015, now abandoned.

(60) Provisional application No. 62/023,052, filed on Jul. 10, 2014.

(51) Int. Cl.
*A61B 5/00*    (2006.01)

(52) U.S. Cl.
CPC .......... *A61B 5/0075* (2013.01); *A61B 5/6817* (2013.01); *A61B 5/0086* (2013.01)

(58) Field of Classification Search
CPC .............................. A61B 5/6817; A61B 5/0075
USPC ................................................ 600/188, 200
See application file for complete search history.

(56) References Cited

U.S. PATENT DOCUMENTS

| 6,110,106 | A | 8/2000 | MacKinnon et al. | |
| 6,379,920 | B1* | 4/2002 | El-Sayed | C12Q 1/02 435/29 |
| 7,586,618 | B2 | 9/2009 | Marks et al. | |
| 7,623,908 | B2 | 11/2009 | Boppart et al. | |
| 7,725,169 | B2 | 5/2010 | Boppart et al. | |
| 7,787,129 | B2 | 8/2010 | Zysk et al. | |

(Continued)

FOREIGN PATENT DOCUMENTS

WO    WO 02/088705    11/2002    ............. G01N 33/00

OTHER PUBLICATIONS

American Academy of Pediatrics, *Pediatrics*, Clinical Practice Guideline, "Otitis Media with Effusion," vol. 113. No. 5, pp. 1412-1429 (May 2004).

(Continued)

*Primary Examiner* — Si Ming Ku
(74) *Attorney, Agent, or Firm* — Sunstein LLP (57) ABSTRACT

Methods and apparatus for identifying microbiological constituents in the middle ear. A spectrometer receives Raman-scattered light from the region of the tympanic membrane and resolves spectral features of the Raman-scattered light. A processor receives the interferometry signal and the Raman signal, and generates a Raman spectrum of the tympanic membrane and material adjacent thereto. In some embodiments of the invention, low-coherence light and substantially monochromatic excitation light are directed onto a tympanic membrane of the ear of a person via an otoscopic tip that abuts the ear canal. An interferometer combines scattered low-coherence light from the ear tissue with a reference signal to generate an interferometric signal.

7 Claims, 7 Drawing Sheets

(56) References Cited

U.S. PATENT DOCUMENTS

| | | | |
|---|---|---|---|
| 8,115,934 B2 * | 2/2012 | Boppart | G01B 9/02014 356/479 |
| 2003/0082104 A1 | 5/2003 | Mertelmeier | |
| 2004/0181128 A1 | 9/2004 | Masters | |
| 2006/0276709 A1 | 12/2006 | Khamene et al. | |
| 2010/0208252 A1 * | 8/2010 | Marks | G01J 3/4531 356/301 |
| 2011/0224493 A1 | 9/2011 | Oyadiran et al. | |

OTHER PUBLICATIONS

Hall-Stoodley et al., "Direct Detection of Bacterial Biofilms on the Middle-Ear Mucosa of Children with Chronic Otitis Media," *JAMA-J. Am. Med. Assoc.*, vol. 296, No. 2, pp. 202-211 (Jul. 2006).

Huang et al., Integrated Raman spectroscopy and trimodal wide-field imaging techniques for real-time in vivo tissue Raman measurements at endoscopy, *Opt. Lett.*, vol. 34, No. 6, pp. 758-760 (Mar. 2009).

Jung et al., "Handheld Optical Coherence Tomography Scanner for Primary Care Diagnostics," *IEEE T Bio.-Med. Eng.*, vol. 58, No. 3, pp. 741-744 (Mar. 2011).

Khan et al., "Depth-sensitive Raman spectroscopy combined with optical coherence tomography for layered tissue analysis," *J. BioPhotonics*, vol. 7, No. 1-2, pp. 77-85 (2014).

Liu et al., "Fiber-based combined optical coherence and multiphoton endomicroscopy," *J. Biomed. Opt.*, vol. 16, No. 3, pp. 036010-1-036010-4 (Mar. 2011).

Longo et al., "Bi modal Approach Using Spectroscopy and Digital Imaging to assist Otitis Media Diagnosis," *Northeast Bioengineering Conference (NEBEC)*, 3 pages (Apr. 2014).

Marks et al., "Molecular Species Sensitive Optical Coherence Tomography using Coherent Anti-Stokes Raman Scattering Spectroscopy," *Proc. SPIE*, vol. 4956, pp. 9-13 (2003).

Marks et al., "Inverse scattering for frequency-scanned full-field optical coherence tomography," *J. Opt. Soc. Am. A*, vol. 24, No. 4, pp. 1034-1041 (Apr. 2007).

Naumann, "Infrared and NIR Raman spectroscopy in medical microbiology," *SPIE Proc.*, vol. 3257 (Apr. 1998).

Nguyen et al., "Non-invasive optical interferometry for the assessment of biofilm growth in the middle ear," *Biomedical Opt. Exp.*, vol. 1, No. 4, pp. 1104-1116 (Nov. 2010).

Nguyen et al. "Noninvasive in vivo optical detection of biofilm in the human middle ear," *P. Natl. Acad. Sci. USA*, vol. 109, No. 24, pp. 9529-9534 (Jun. 2012).

Patil et al., "Combined Raman spectroscopy and optical coherence tomography device for tissue characterization," *Opt. Lett.*, vol. 33, No. 10, pp. 1135-1137 (May 2008).

Pitris et al., "High-Resolution Imaging of the Middle Ear With Optical Coherence Tomography," *A Feasibility Study*, vol. 127, pp. 637-642 (2001).

Reed et al., "Gradient-index fiber-optic microprobes for minimally invasive in vivo low-coherence interferometry," *Opt. Lett.*, vol. 27, No. 20, pp. 1794-1796 (Oct. 2002).

Shelton et al., "Optical coherence tomography for advanced screening in the primary care office," *J. Biophotonics*, pp. 1-9 (Apr. 2013).

Shim et al., "Study of Fiber-Optic Probes for in Vivo Medical Raman Spectroscopy," *Applied Spectrosc.*, vol. 53, No. 6, pp. 619-627 (1999).

Sorrell et al., "Bacteria Identification of Otitis Media With Fluorescence Spectroscopy," *Laser Surg. Med.*, vol. 14, pp. 155-163 (1994).

Takata et al. "Evidence Assessment of the Accuracy of Methods of Diagnosing Middle Ear Effusion in Children With Otitis Media With Effusion," *Pediatrics*, vol. 112, No. 6, pp. 1379-1387 (Dec. 2003).

Upile et al., Meeting report, "At the frontiers of surgery: review," *Head and Neck Oncology*, 23 pages (2011).

Wagner et al., "Combined use of confocal laser scanning microscopy (CLSM) and Raman microscopy (RM): Investigations on EPS—Matrix," *Water Res.*, vol. 43, pp. 63-76 (2009).

Xi et al., "High-resolution three-dimensional imaging of biofilm development using optical coherence tomography," *J. Biomed. Opt.*, vol. 11, No. 3, pp. 034001-1-034001-6 (May/Jun. 2006).

Zysk et al., "Computational methods for analysis of human breast tumor tissue in optical coherence tomography images," *J. Biomed. Opt.*, vol. 11, No. 5, pp. 054015-1-054015-7 (Sep./Oct. 2006).

* cited by examiner

HANDHELD DEVICE FOR IDENTIFICATION OF MICROBIOLOGICAL CONSTITUENTS IN THE MIDDLE EAR

The present application is a divisional of currently pending U.S. Ser. No. 14/722,344, filed May 27, 2015, and, through that application, claims the priority of U.S. Provisional Patent Application Ser. No. 62/023,052, filed Jul. 10, 2014. Both of the foregoing applications are incorporated herein by reference.

This invention was made with government support under Grant R01 EB013723, awarded by the National Institutes of Health. The Government has certain rights in the invention.

TECHNICAL FIELD

The present invention relates to apparatus and methods for non-invasive otoscopy, and, more particularly, to apparatus and methods for optical identification of the microbiological origins of a presenting ear infection.

BACKGROUND ART

Otitis media (OM) is a highly prevalent disease, in fact, it is the most common childhood illness treated by pediatricians. While more than 75% of children have at least one episode of OM by age 3, and many have recurrent or chronic OM, a major impediment to effective treatment is the distinction of bacterial from viral infections. Failure to distinguish bacterial from viral infection results in overprescription of, and overexposure to, antibiotics, and, more generally, to ineffective treatment.

An effective point-of-care diagnostic modality to distinguish microbiological origins of ear infections would be highly desirable, both in the developed and developing world.

Portable systems and handheld optical scanners incorporating low-coherence interferometry (LCI) (FIG. 1) and optical coherence tomography (OCT) imaging technology with color video imaging have been described for detecting and monitoring middle-ear biofilms in humans, based on the microstructural features of the TM and any associated biofilm. The use of OCT for non-invasively imaging ear tissue was taught in U.S. Pat. No. 8,115,934, entitled "Device and Method for Imaging the Ear using Optical Coherence Tomography," and incorporated herein by reference. Further LCI and OCT systems are discussed in copending U.S. patent application Ser. No. 14/303,134, filed Jun. 12, 2014, also incorporated herein by reference. This technology has been used to non-invasively detect the presence of middle-ear biofilms in adults and children. However, current screening and diagnostic technology based on OCT and video imaging are unable to identify the microbiological origin of ear infections. Therefore, there is a clear need for a point-of-care diagnostic to determine whether an infection is bacterial or viral, and furthermore, to distinguish the bacterial species present in order to guide treatment.

Four bacteria are known to account for 80-90% of middle infections: *Streptococcus pneumonia* (SP), *Haemophilus influenza* (HI), *Moraxella catarrhalis* (MC), and *Staphylococcus aureus* (SA). One diagnostic modality that has been shown to identify these bacterial species with some degree of specificity is fluorescence spectroscopy, as described by Sorrell et al., *Bacterial Identification of Otitis Media with Fluorescence Spectroscopy, Laser in Surgery & Med.*, vol. 14, pp. 155-63 (1994), incorporated herein by reference. Other diagnostic modalities that have been shown to provide for identification of bacterial species are based on distinguishing vibrational modes in the infrared, applying such modalities as infrared absorption spectroscopy using Fourier-transform infrared (FTIR) techniques, and Raman spectroscopy, with excitation in various spectral regimes. Early work was reviewed in Naumann, *Infrared and NIR Raman Spectroscopy in Medical Microbiology, Proc. SPIE 3257, Infrared Spectroscopy: New Tool in Medicine*, 245, (1998), incorporated herein by reference. A more recent review of Raman spectroscopic techniques applied to microbiological constituents may be found in Krafft et al. (Popp), *Raman and CARS microspectroscopy of cells and tissues, Analyst*, vol. 134, pp. 1046-57 (2009), also incorporated herein by reference.

Application of near-infrared Raman spectroscopy to material aspirated from the ear, is discussed in U.S. Pat. No. 6,379,920 (to El-Sayed, et al.), incorporated herein by reference. In the prior art, however, application of Raman spectroscopy to infected material in the middle ear has required withdrawal of a biological sample for analysis in the laboratory.

A hand-held system, combining Raman scattering analysis with OCT (RS-OCT), has been reported, for characterizing skin tissue in vivo, by Patil et al., *"Combined Raman spectroscopy and optical coherence tomography device for tissue characterization,"* Opt. Lett., vol. 33 pp. 1135-37 (2008), which is incorporated herein by reference. The Patil system, however, uses galvo scanners for transverse beam scanning, something that is particularly impractical for in vivo scattering diagnostics within the ear.

The use of optical coherence tomography (OCT) imaging technology in conjunction with multiphoton microscopy, with both an OCT source and an excitation beam coupled to imaged tissue via a single double-clad fiber has been described by Liu et al., *"Fiber-Based Combined Optical Coherence and Multiphoton Endomicroscopy,"* J. Biomed. Opt., vol. 16, 036010 (March 2011), which is incorporated herein by reference. Liu, however, uses the same femtosecond fiber laser source both for Fourier-domain optical coherence microscopy (OCM) and as the excitation source for multiphoton microscopy, thereby imposing various operational limitations that are undesirable in the context of middle-ear diagnostics. Advantages of dual-clad fibers for such applications have been known for some time, as discussed, for example, in Shim et al., *Study of Fiber-Optic Probes for in Vivo Medical Raman Spectroscopy, Appl. Spectrosc.*, vol. 53, pp. 619-27 (1999), incorporated herein by reference. However, such technology has never been suggested in an otoscopic context, because of the anatomical peculiarities of the middle ear, insofar as scattering signals are depth-dependent, and no mechanism is provided, in the prior art, to account for the variation of Raman signal with placement. Khan, *"Depth-sensitive Raman spectroscopy combined with optical coherence tomography for layered tissue analysis,"* J. Biophotonics, vol. 7, pp. 77-85 (published online 29 Jan. 2013) teaches co-registered OCT and Raman spectroscopy, but fails to teach a practical method for reproducibly coupling excitation into the ear and scattering into a spectrometer. The prior art provides no independent way to assess where the Raman probe is actually sampling. Thus, for well over a decade, a solution has eluded practitioners as to how the specificity of Raman diagnostic techniques could be brought to bear on inner-ear problems.

Non-invasive imaging of various features of the middle ear, using methods of low-coherence interferometry (LCI) or optical coherence tomography (OCT) has been described in the prior art, as in U.S. Pat. No. 8,115,934 ("Boppart '934", incorporated herein by reference) and elsewhere. Low-coherence interferometry (LCI) is a well-known optical coherence technique capable of measuring one-dimensional depth-resolved tissue structure with a typical resolution of several microns. Optical Coherence Tomography (OCT) combines LCI with a lateral scanning mechanism to generate cross-sectional images of biological tissues. LCI and OCT are non-invasive imaging techniques, typically using near-infrared light to obtain structural information from human tissues in vivo. Further information regarding the application of OCT to imaging ear tissue may be found in the following references, all of which are incorporated herein by reference:

- Xi et al., "High-resolution three-dimensional imaging of biofilm development using optical coherence tomography," J. Biomed. Opt., vol. 11, pp. 11(3):134001-1-134001-6, (2006).
- Pitris et al., "High-resolution imaging of the middle ear with optical coherence tomography: a feasibility study," Arch. Otolaryngology—Head & Neck Surg., vol. 127, pp. 637-642, (2001).
- Jung et al., "Handheld Optical Coherence Tomography Scanner for Primary Care Diagnostics," IEEE Trans. Biomed. Eng., vol. 58, pp. 741-44, (2011).
- Nguyen et al., "Noninvasive in vivo optical detection of biofilm in the human middle ear," Proc. Nat. Acad. Of Sciences, vol. 109, pp. 9529-34, (May 29, 2012), ("Nguyen 2012").
- Shelton et al., "Optical coherence tomography for advanced screening in the primary care office," J. Biophotonics, DOI: 10.1002/jbio.201200243, (Apr. 18, 2013), hereinafter, "Shelton (2013)."

Figure 1A:
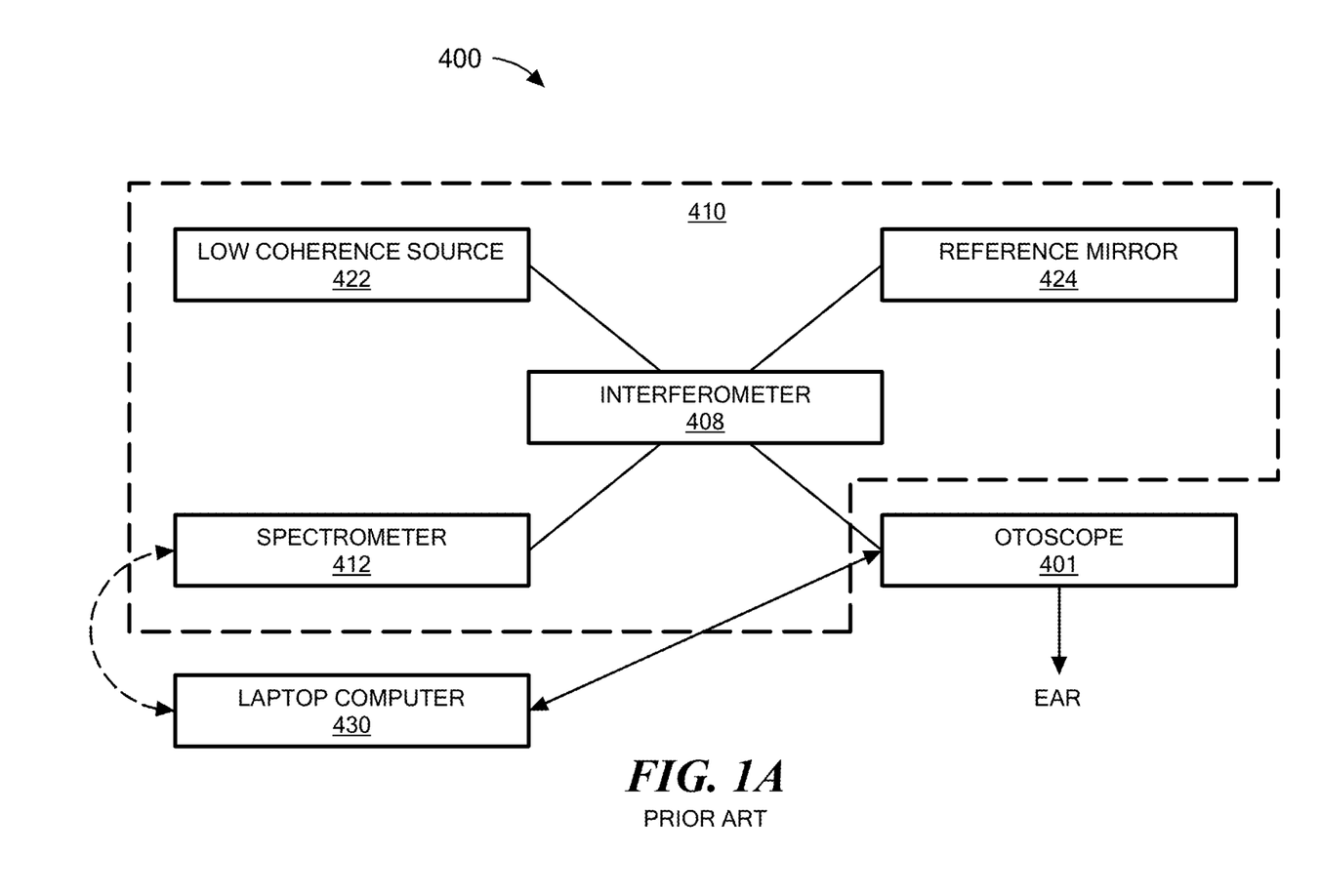
Figure 1B:
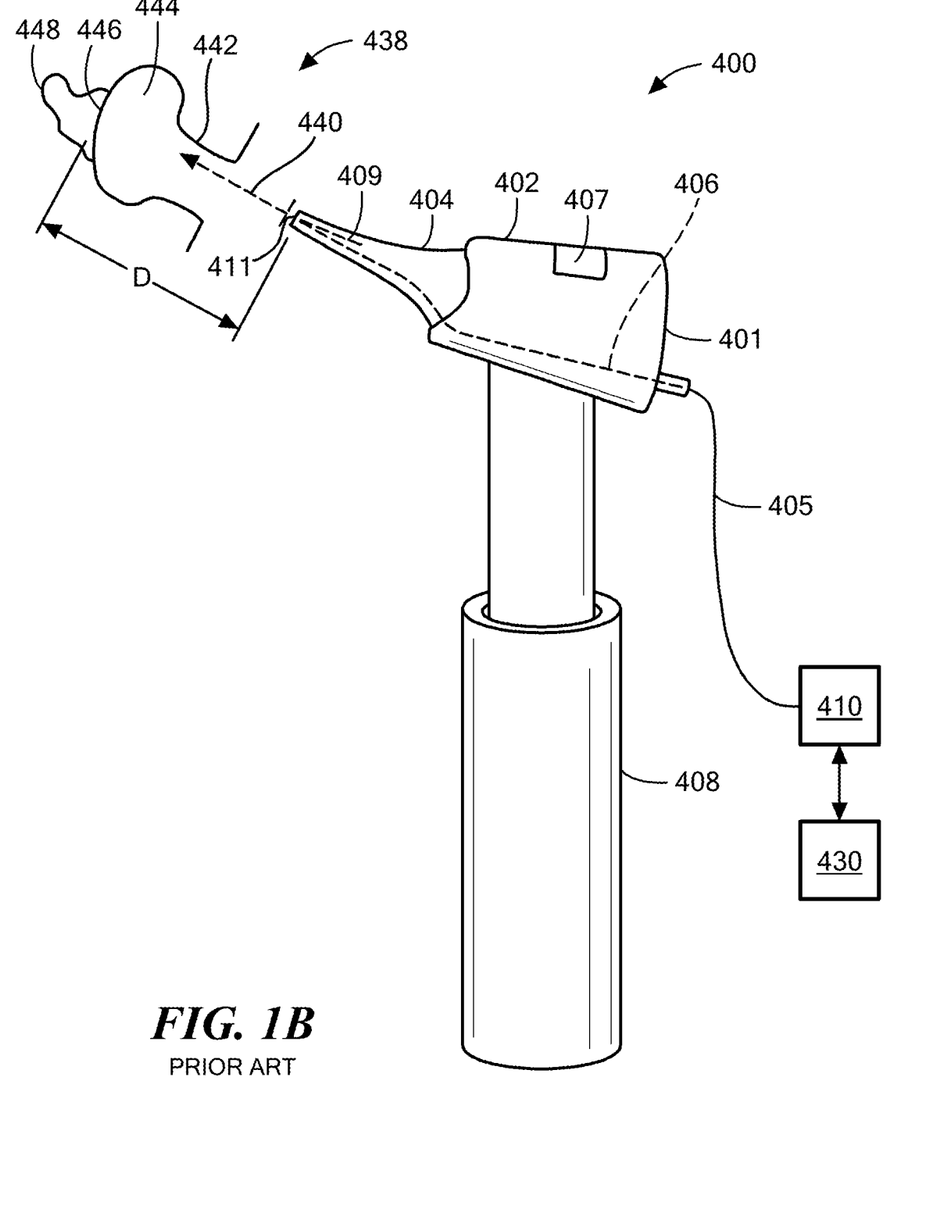
FIG. 1B depicts a prior art device for imaging the middle ear using OCT.

Salient features of a prior art LCI/OCT otoscope are described with reference to FIG. 1A, which appears as FIG. 10 in the Boppart '934 patent. A device 400 for imaging the ear using optical coherence tomography includes a core imaging unit 410 in communication with a core software unit 430, which may be a laptop computer, for example. The core imaging unit 410 may be integrated within the device 400 so as to provide a compact portable instrument. The core imaging unit 410 is in communication with the core software unit 430, as shown in FIG. 1B.

The device 400 can image visible structures (i.e., structures that can be seen with the naked eye), such as the tympanic membrane, with enough accuracy to account for slight variations or movement in those structures. Additionally, the device 400 can image structures which are not visible to the naked eye, such as middle ear structures behind the tympanic membrane in order to search for tissue, such as biofilms.

In accordance with the operation of LCI or OCT devices, light emitted by a low-coherence source 422 is incident upon ear tissue via otoscope 401, and is combined with a reference beam, such as derived via reference mirror 424, in interferometer 408, thereby gating a detection signal to a tightly localized scattering window. The reference beam may share a common path with the signal beam and be reflected, for example, from a window in the signal beam path. Low-coherence source 402 is swept in wavelength, and the interferometer output may be wavelength-resolved by spectrometer 412.

The imaging device 400 typically includes devices which can form a direct line of sight from the tympanic membrane to the outside of the ear, such as an ear speculum, an otoscope 401, or a pneumatic otoscope.

The prior art imaging device 400 is capable of non-invasively imaging inside the patient's ear canal and more specifically, non-invasively imaging the patient's middle ear. At least a portion of the device is adapted for insertion into the patient's ear canal, allowing for non-invasive imaging of the patient's ear canal and or middle ear. The prior art imaging device 400 may have a fiber based device 406 connected with or integrated with the otoscope 401, as shown in FIG. 1B. The fiber based device 406 includes an optical fiber acting as a light guide. When the otoscope 401 is placed near or within a patient's ear canal 442, light from the inner or middle-ear 444 is carried through the fiber based device 406 to the core imaging unit 410. The fiber based device 406 is connected with the otoscope 401.

Fiber-based device 406 may include a fiber-optic OCT probe which can be used to generate OCT signals, LCI signals, or both OCT and LCI signals. The resulting OCT data facilitates the detection of tissue structures including the eardrum 446, ossicles 448, and the presence of a biofilm.

Figure 2A:
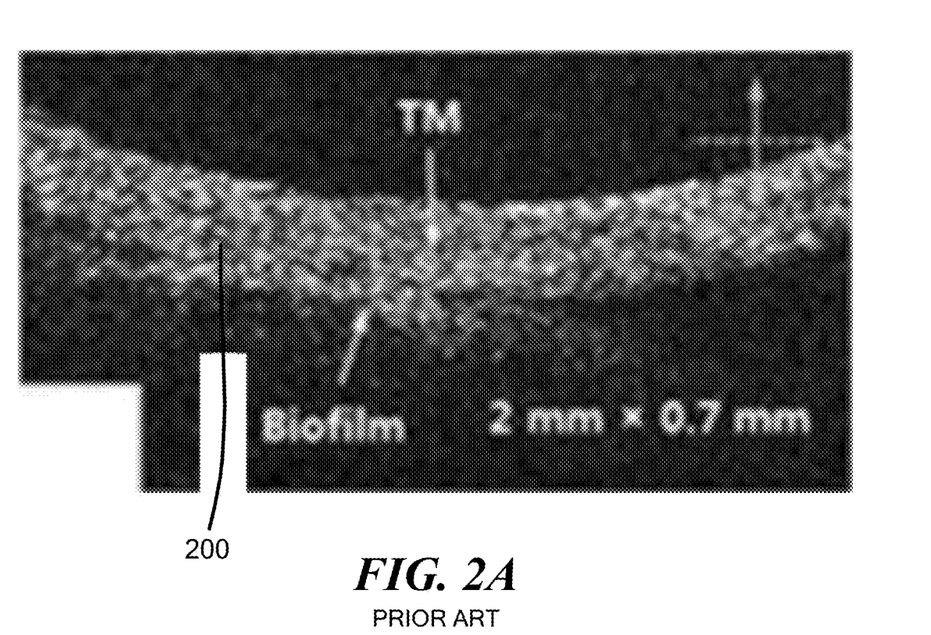
FIGS. 2A and 2B show prior art OCT images of the tympanic membrane and associated biofilm within the middle ear of a patient.
Figure 2B:
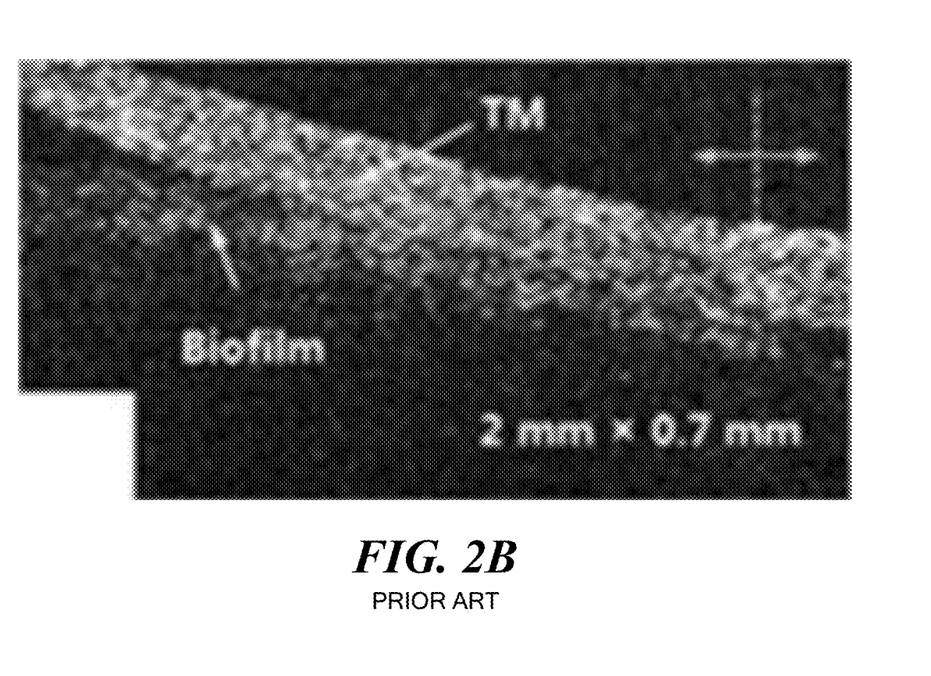

FIGS. 2A and 2B (FIGS. 4C and 4D in Shelton (2013)), show images of a tympanic membrane TM with an accompanying biofilm 200 from a patient with chronic otitis media.

The foregoing art, however, is incapable of effective point-of-care diagnostic distinction among microbiological origins of ear infections, and, thus, an instrument with such capability would be highly desirable, both in the developed and developing world.

Summary of Embodiments of the Invention

In accordance with embodiments of the invention, apparatuses and methods are provided for diagnosing and identifying microbiological material within the ear of a person. An otoscopic diagnostic system for jointly performing those functions has a. a source of substantially monochromatic excitation light;
b. an otoscopic tip for abutment with the ear canal for directing the substantially monochromatic excitation light to a tympanic membrane of an ear of a person and for collecting Raman scattered light from the tympanic membrane and material behind the tympanic membrane and from material adjacent to the tympanic membrane;
c. a spectrometer for receiving the Raman-scattered light, for resolving spectral features of the Raman-scattered light, and for generating a Raman signal; and
d. a processor for receiving the Raman signal, and for generating therefrom a Raman spectrum of the tympanic membrane and the material behind the tympanic membrane and the material adjacent to the tympanic membrane.

In accordance with alternate embodiments of the invention, the otoscopic tip may be an earbud, or a speculum coupled to a hand-held otoscope. The substantially monochromatic excitation light may be guided to the ear canal via a first optical fiber. The otoscopic diagnostic system in accordance with claim 1, wherein the source of substantially monochromatic excitation light may be disposed within a core imaging unit, as may the spectrometer.

In accordance with other embodiments of the invention, the first optical fiber may be a dual-cladding fiber having a central core, and the substantially monochromatic excitation light may be guided to the ear canal via the central core of the dual-cladding fiber. The Raman-scattered light may be guided to the spectrometer via cladding of the dual-cladding fiber. The otoscopic diagnostic system may have first focusing optics for coupling the low-coherence light to a vicinity of the tympanic membrane of the person, and the first focusing optics may include a first micro-gradient-index lens. The first focusing optics may also collect the Raman-scattered light.

In yet other embodiments of the invention, the otoscopic diagnostic system may also have an ear bud coupled to a tip of a hand-held otoscope, with the ear bud encompassing a portion of the first optical fiber.

In still further embodiments of the invention, the otoscopic diagnostic system may also have a source of low-coherence light and an interferometer for combining the scattered low-coherence light from the ear tissue with a reference signal derived from the low-coherence light for generating an interferometry signal. In such embodiments of the invention, the processor is adapted for receiving both the interferometry signal and the Raman signal, and for generating therefrom a Raman spectrum of the tympanic membrane and material in the vicinity thereof.

In accordance with other embodiments of the invention, the source of low-coherence light may be a superluminescent diode, and the low-coherence light may include an infrared component. Second focusing optics may be provided for coupling the low-coherence light to a vicinity of the tympanic membrane of the person.

In accordance with another aspect of the present invention, an otoscopic tip is provided for insertion into an ear canal of a person. The otoscopic tip has an earbud assembly adapted for insertion into an ear canal, and focusing optics adapted for directing excitation to the vicinity of the tympanic membrane of the person via the ear bud and through the ear canal and for collecting Raman-scattered excitation from the vicinity of the tympanic membrane of the person.

The earbud assembly may be coupled to a hand-held otoscope. The low-coherence light and the excitation light may be coupled from respective remote sources disposed remotely with respect to the hand-held otoscope. Both the low-coherence light and the excitation light are coupled from the remote source via optical fiber. One or both of the first and second focusing optics may include a micro-gradient-index lens.

In accordance with yet another aspect of the present invention, a method is provided for characterizing at least one of a middle ear fluid, a middle ear effusion, and a biofilm adjacent to a tympanic membrane of a person. The method has steps of:
  a. illuminating the tympanic membrane with a broadband optical beam;
  b. interfering light scattered by the tympanic membrane with a reference beam derived from the broadband optical beam to generate an interferometric signal;
  c. illuminating the tympanic membrane with a monochromatic excitation beam;
  d. coupling Raman-scattered light from the tympanic membrane to a spectrometer;
  e. dispersing the Raman-scattered light to obtain a Raman spectrum characterizing the Raman-scattered light;
  f. ascertaining a first specified characteristic of any material adjacent to the tympanic membrane on the basis of the interferometric signal; and
  g. ascertaining a second specified characteristic of any material adjacent to the tympanic membrane on the basis of the Raman spectrum signal.

The first specified characteristic may be a measure of geometrical thickness of the tympanic membrane and any attached biofilm, or a measure of at least one of viscosity and turbidity. Alternatively, the first specified characteristic may be an image. The material adjacent to the tympanic membrane of the person may be at least one of a biofilm and effusion material.

The second specified characteristic may be at least one of a bacterial type, a viral type and a fungal type, and the second specified characteristic may also be an identification of an extracellular polymeric substance.

BRIEF DESCRIPTION OF THE DRAWINGS

The foregoing features of the invention will be more readily understood by reference to the following detailed description, taken with reference to the accompanying drawings, in which:

FIG. 1A shows a schematic diagram of salient components of the optical system of a prior art LCI otoscope, while

FIG. 5A shows plots of a Raman spectrum of the bacterial strain of *S. pneumoniae* and a control spectrum, while

DETAILED DESCRIPTION OF EMBODIMENTS OF THE INVENTION

Definitions: As used herein, or in any appended claims, the term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The terms "object," "sample," and "specimen" shall refer, interchangeably, to a tangible, non-transitory physical object capable of being rendered as an image.

When used to modify terms such as "beam," "pulse," etc., the terms "sample" and "signal" are used herein interchangeably.

The term "scattering medium," as used herein and in any appended claim, shall mean a medium in which an incident electromagnetic wave, of a wavelength range pertinent to the context under discussion, shall be characterized by a mean free path to scatter that is substantially shorter than the dimension of the medium in the propagation direction of the incident electromagnetic wave.

The term "scattering biological tissue," as used herein and in any appended claim, shall mean an organized ensemble of interconnected cells of an organism that has the optical properties associated with a scattering medium, as defined above.

As used herein, and in any appended claims, the term "vicinity of the tympanic membrane" shall be understood broadly as encompassing the tympanic membrane (TM) itself, as well as the region adjacent to the TM and behind the TM, the middle-ear space, any adjacent biofilm, or effusion, etc.

The term "low-coherence" (or "broadband," as used interchangeably herein) applies to illumination, or to its source, for which the coherence length is shorter than 30 μm, and/or for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source need not be fixed in time, indeed, the wavelength of the source may be swept in time.

In accordance with embodiments of the present invention, a fiber-based otoscopic diagnostic system is provided as now described with reference to FIG. 3A where the fiber-based otoscopic diagnostic system is designated generally by numeral 300. Low-coherence light (as defined above) is generated by a low-coherence source 302 (also referred to herein as an "LCI source"), which may be a superluminescent diode, for example, and which may have wavelengths in the visible portion of the electromagnetic spectrum, and/or in the infrared portion of the spectrum. In a preferred embodiment of the invention, low-coherence source 302 emits light centered at the infrared wavelength of 840 nm, with a bandwidth of 45 nm, thereby providing 5 μm axial resolution in tissue.

Low-coherence light from LCI source 302 is split by coupler 304 (which may be a 50/50 coupler, for example) into a sample arm 306 (referred to herein, equivalently, as a "signal arm") and a reference arm 308, both implemented in waveguides, and, preferably, in optical fibers. The low-coherence light in sample arm 306 is coupled via an otoscopic tip 310 into the ear canal of a subject, typically a human, although the instant invention may also be advantageously applied to other animals. In FIG. 3A, otoscopic tip 310 is shown as a freestanding ear bud, however it is to be understood that any otoscopic tip may be employed within the scope of the present invention. Thus, for example, a speculum 404 (shown in FIG. 1B), which may be attached to a handheld otoscope 408 (shown in FIG. 1B), may serve as otoscopic tip 310 in other embodiments of the invention.

Scattering from the TM (or other tissue or material within the ear) is returned, via sample arm 306 and coupler 304, and interfered with light in reference arm 308, similarly returned, by reflection at mirror 312, via coupler 304, with the interference signal analyzed at LCI spectrometer 314, an example being a modular spectrometer available from Ocean Optics of Dunedin, Fla. Alternatively, other LCI or OCT modes may be employed, although maintenance of a stationary reference arm 308 and spectral resolution of depth-resolved axial scan data is a preferred embodiment, in which an acquisition rate of 1000 axial scans per second may be supported.

A source 316 of substantially monochromatic excitation light serves as a second source of illumination of the sampled region, and is otherwise referred to herein as a "Raman source." Raman source 316 emits excitation light (which, in that it gives rise to Raman scattering, may be referred to herein as Raman excitation light) that is also coupled to be incident upon tissue in the ear of the patient. The Raman excitation light may be light at 785 nm, using a diode laser as Raman source 316. Light at 785 nm is typically preferred for Raman spectroscopy, in that light at substantially shorter wavelengths (such as the 552 nm light of a frequency-doubled YAG laser, for example) gives rise to fluorescence, thereby confounding the Raman spectrum. However, the wavelength of the Raman excitation light is not limited within the scope of the present invention. Raman excitation light is scattered by a process of inelastic Raman scattering, resulting in scattering emission at longer wavelengths (Stokes emission), displaced by frequency (or, equivalently, wavelength) shifts that, together, constitute a molecular vibrational signature of the scattering medium.

The Raman excitation light is conveyed from source 316 into the patient's ear via core 322 of Raman spectroscopy fiber 320, where Raman spectroscopy fiber 320 is preferably a dual-cladding fiber, with an inner cladding 324 and an outer cladding 326. Raman spectroscopy fiber 320 enters the patient's ear via otoscopic tip 310, which, in the embodiment of FIG. 3A, is an earbud, although other otoscopic tips are within the scope of the present invention.

Raman scattered light from the sample tissue (such as tympanic membrane TM, shown in FIGS. 2A and 2B), and from biofilm 200 (shown in FIG. 2A) or effusion, is coupled into the inner cladding 324 (as further discussed infra) and guided back to coupler where the Raman scattered light is coupled out into multimode fiber MM in which it is guided, via filter 328, to a Raman spectrometer 330. Filter 328 serves to remove any residual excitation light from light returned via inner cladding 324. It is to be understood that coupling via multimode fiber MM is described by way of example, but that the Raman scattered light may be coupled to Raman spectrometer 330 in any other way, within the scope of the present invention. Referring to FIG. 3B, Raman excitation light guided via inner core 322 of Raman spectroscopy fiber 320 towards the ear is coupled via a lens 336, preferably a graded index (GRIN) lens, to a focal region 332 (shown in FIG. 3C) within the tissue of a person's ear, and Raman-scattered light, scattered by the focal region 332, is coupled, via lens 336, into inner cladding 324 of the Raman spectroscopy fiber 320. The Raman excitation light is preferably focused into the middle ear, roughly behind the TM. In certain embodiments of the invention, no lens is employed at the distal end of Raman spectroscopy fiber 320.

Figure 3A:
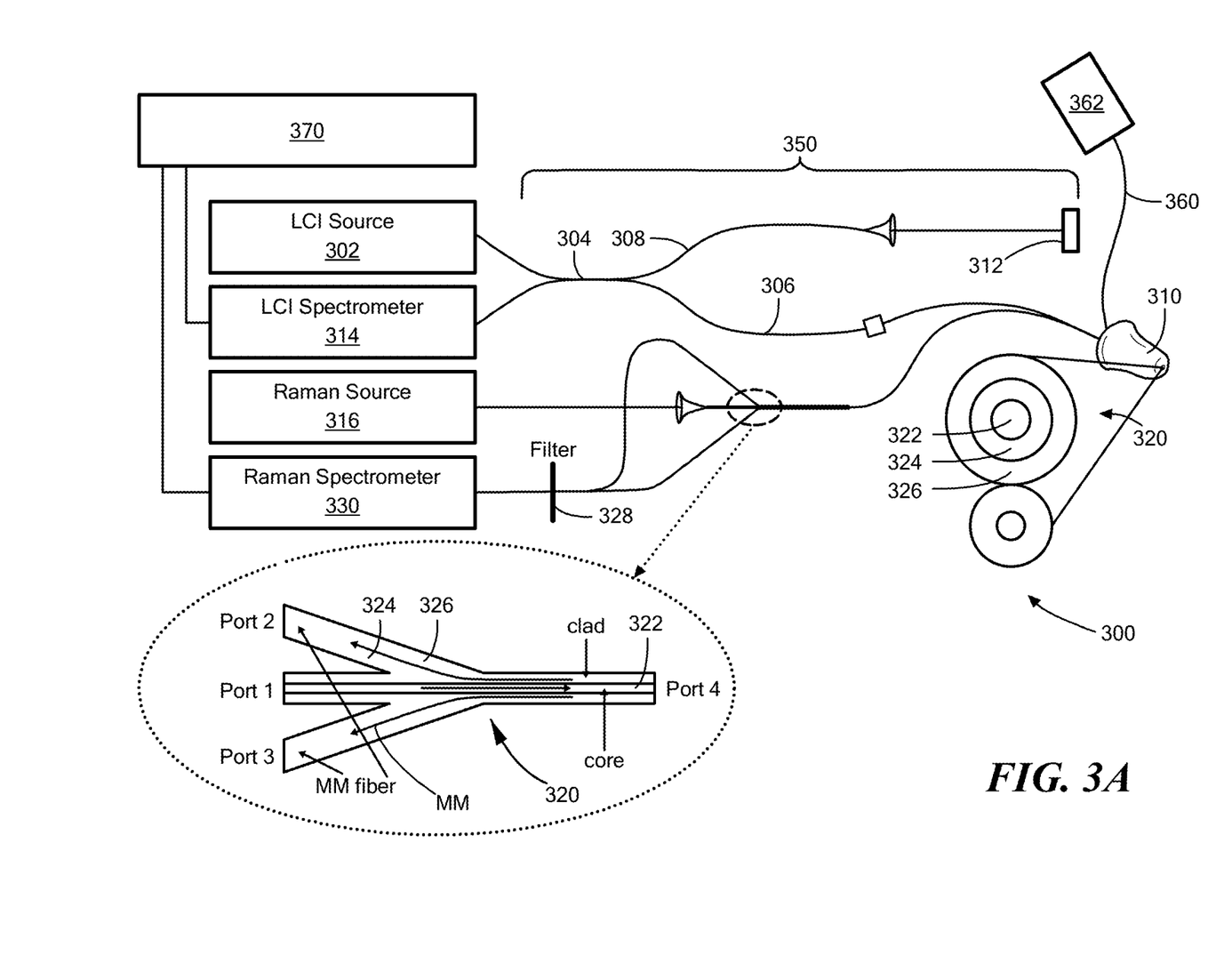
FIG. 3A is a schematic depiction of an otoscopic diagnostic system in accordance with an embodiment of the present invention, while FIGS. 3B and 3C, respectively, show cross sections of GRIN lenses for coupling Raman excitation and scattering, and LCI sample and scattering beams, to and from regions within the ear.
Figure 3B:
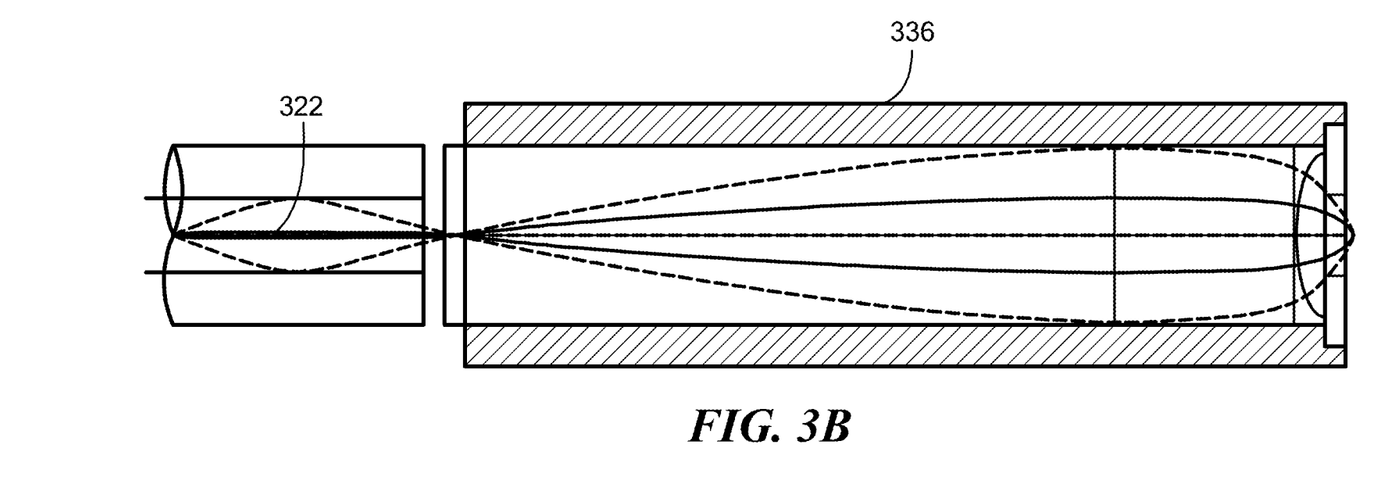
Figure 3C:
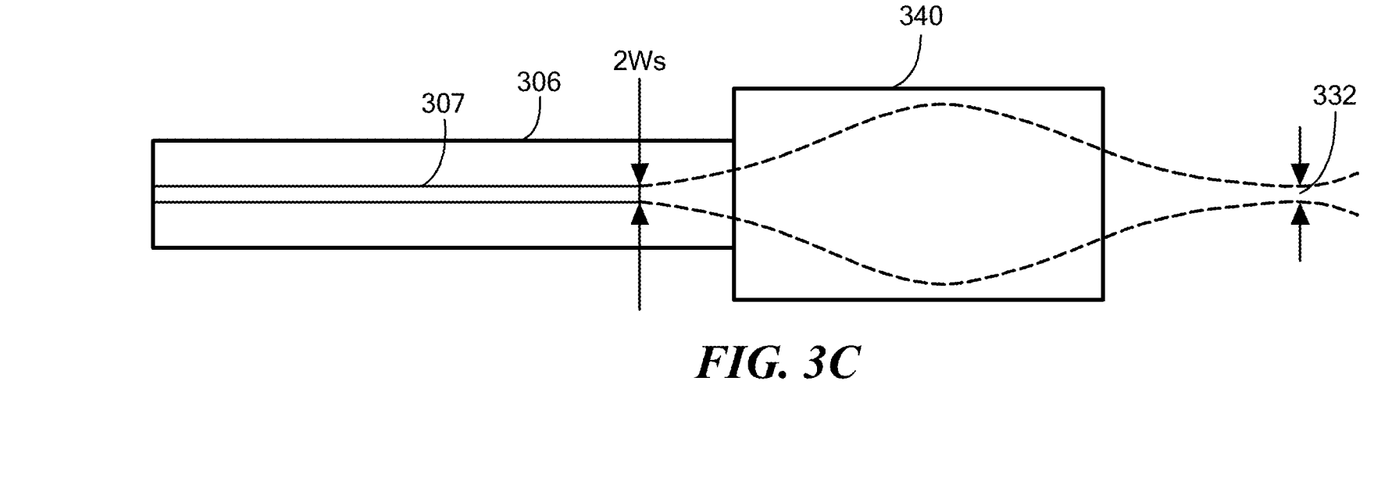

Referring to FIG. 3C, low-coherence light (the LCI beam) in core 307 of sample arm 306 propagating towards the ear is coupled via a lens 340, preferably a graded index (GRIN) lens, to a focal region 332 of tissue, and low-coherence light scattered by the focal region 332 is coupled, via lens 340, back into core 307 of sample arm 306. The LCI beam is focused immediately behind the TM, in the middle ear. Backscattered light from the TM and any middle ear biofilm or effusion is thus collected by and guided back to the interferometer (designated generally by numeral 350 in FIG. 3A) constituted by the sample arm 306, reference arm 308, and coupler 304. In certain embodiments of the invention, no lens is employed at the distal end of sample arm 306.

Integration of sample arm 306 and Raman spectroscopy fiber 320 into a single otoscopic tip 310, such as the ear bud depicted in FIG. 3A, inserted into the patient's ear canal. This significantly reduces motion artifacts, and enables signal averaging over the course of minutes, thereby enhancing Raman signal to noise. Within the scope of the present invention, otoscopic tip 310 may be an ear bud disposed on head gear resembling music ear phones, thereby advantageously improving stability. Images of the TM and attendant tissue, biofilm or effusion, are used, in accordance with the present invention, to guide the positioning/placement of otoscopic tip 310 for Raman signal collection. The LCI beam and Raman excitation beam need not be co-aligned to achieve the desired positioning.

LCI, while less complex and less expensive than OCT, still advantageously provides important depth-resolved structural information about the imaged tissue. It is to be understood that, in the context of the present invention as presently claimed, the term "OCT" shall be understood to encompass the entirety of OCT variants known in the art, or developed in the future, including such variants as swept-source, spectral domain, as well as time domain OCT.

The heretofore described modalities for obtaining depth-resolved images of components and effusions of the middle ear of a person are augmented, in accordance with the present invention, to allow identification, by means of Raman spectral data acquired by Raman spectrometer 330, of microbiological material within the ear. Peaks present in Raman spectra (shown in FIGS. 5A and 5B, for example) provide molecular specificity, which distinct spectral features characterizing bacteria from other cells, and differentiating unique bacterial strains.

In accordance with other embodiments of the present invention, a surface image of the TM may be provided, in concert with the aforesaid Raman and LCI/OCT measurements, by adding an imaging fiber bundle 360 to otoscopic imaging system 300. A low-resolution surface image is obtained by camera 362 for guidance. Alternatively, surface imaging may be performed via free-space, as in traditional otoscopes.

The output of Raman spectrometer 330 is coupled to processor 370, which may be a laptop computer, for example, coupled to both LCI spectrometer 314 and Raman spectrometer 330 via USB interfaces, for example. Processor 370 may interface, via wire or wirelessly, to electronic medical record systems for the upload of clinically-relevant results. Raman spectra, acquired by Raman spectrometer 330 and coupled to processor 370, are automatically compared with a database of known spectra corresponding to bacteria of various sorts and pathological conditions. Bacterial, viral, and fungal conditions may be distinguished within the scope of the present invention, as may sub-types of each of these. Additionally, biofilm-specific substances, such as extracellular polymeric substance (EPS), or others, may be distinguished with Raman signatures. Any algorithms, supervised or unsupervised, such as principal component analysis, artificial neural networks, Bayesian classification, etc. may be employed for spectral analysis within the scope of the present invention.

It is to be understood that, in accordance with certain embodiments of the present invention, there are some circumstances in which Raman spectroscopy of the middle ear may be advantageously performed without contemporaneous LCI or OCT sampling. In those specialized circumstances, embodiments of the invention may be practiced without illumination by low-coherence light.

It is also to be understood that application of low-coherence interferometry or optical coherence tomography need no result in the production of an image, within the scope of the present invention. Either modality may be used, whether on the basis of a single- or multiple-depth scan, to ensure consistent positioning of otoscopic tip 310.

Figure 4:
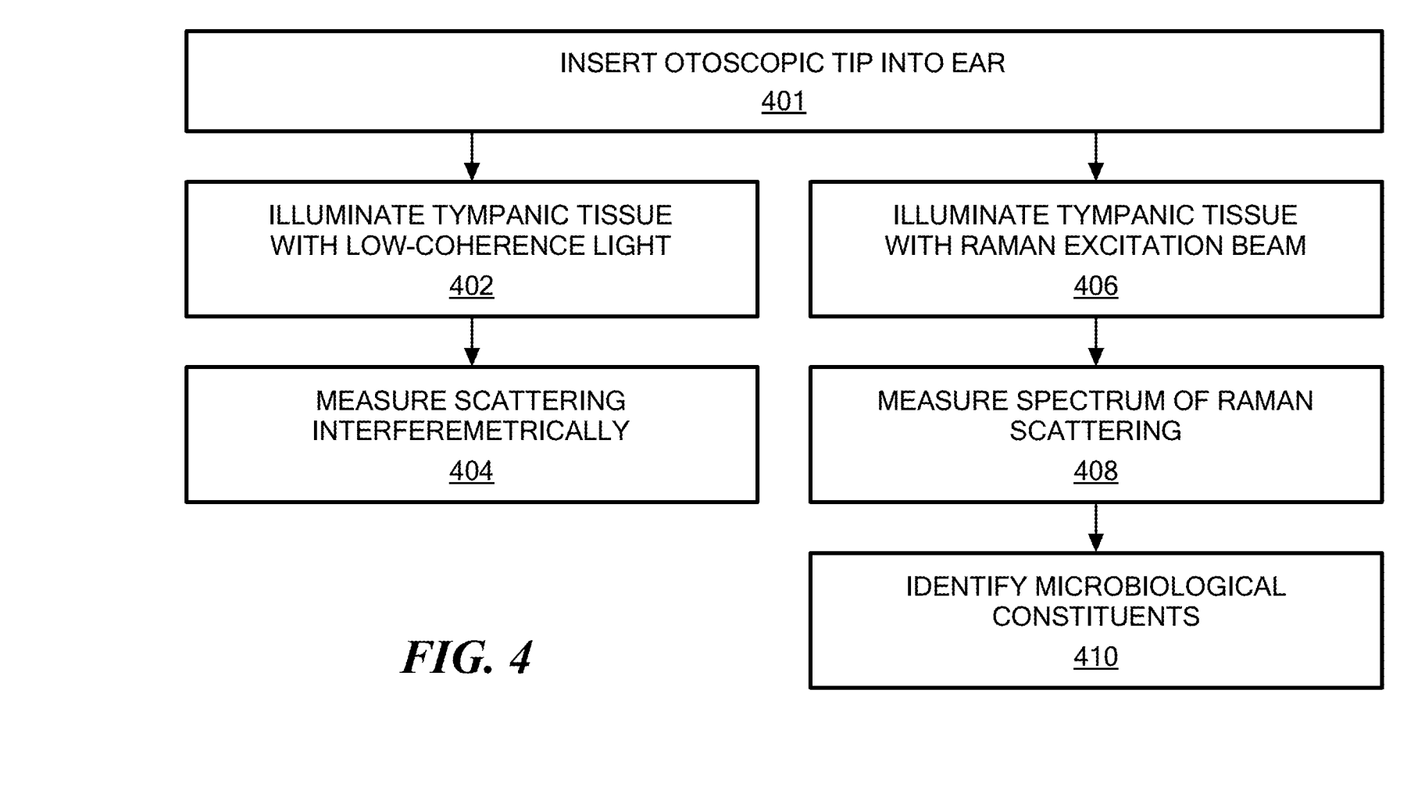
FIG. 4 is a flowchart depicting a process of middle ear characterization, in accordance with an embodiment of the present invention.

FIG. 4 shows a flowchart depicting salient steps in accordance with diagnostic methods of certain embodiments of the present invention. Otoscope tip 310 (shown in FIG. 3A) is inserted into the ear of a patient in step 401. The signal beam derived from low-coherence source 302 (shown in FIG. 1A) is used to illuminate (302) tympanic tissue. Light emitted by low-coherence source 302 is preferably infrared light that penetrates tympanic tissue to a significant depth, including traversing the tympanic membrane completely.

Using LCI or OCT modality, scattering from the path of low-coherence illumination of the tympanic membrane is measured interferometrically (404) as a function of distance into the ear relative to a fiducial reference point. This profile represents the one-dimensional structural scattering information of the middle-ear. Since the axial depth-scan is fast, relative to small lateral movements between the speculum and the ear, multiple axial-scans can be acquired rapidly, corresponding to a specific set of sampling data that can be analyzed by a computer or reconstructed to produce a cross-section type of "image" associated with the continuous trace of these sampled regions. This information facilitates the detection of tissue structures including the eardrum, ossicles, and the presence of a biofilm.

Concurrently or alternatingly with LCI illumination of step 402, tympanic tissue is also illuminated (406) with a Raman excitation beam derived from Raman source 316. The spectrum of collected Raman scattering is measured (408), and microbiological constituents giving rise to the Raman scattering are identified, in step 410.

Figure 5A:
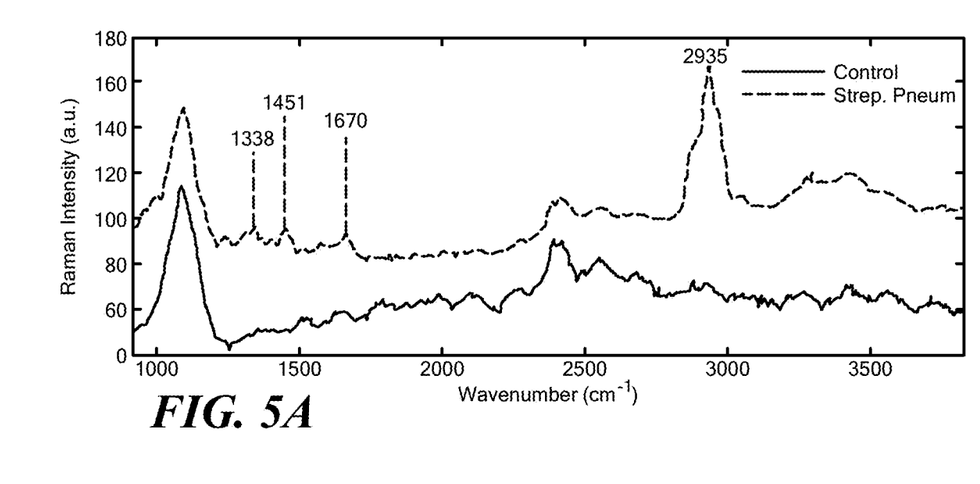
Figure 5B:
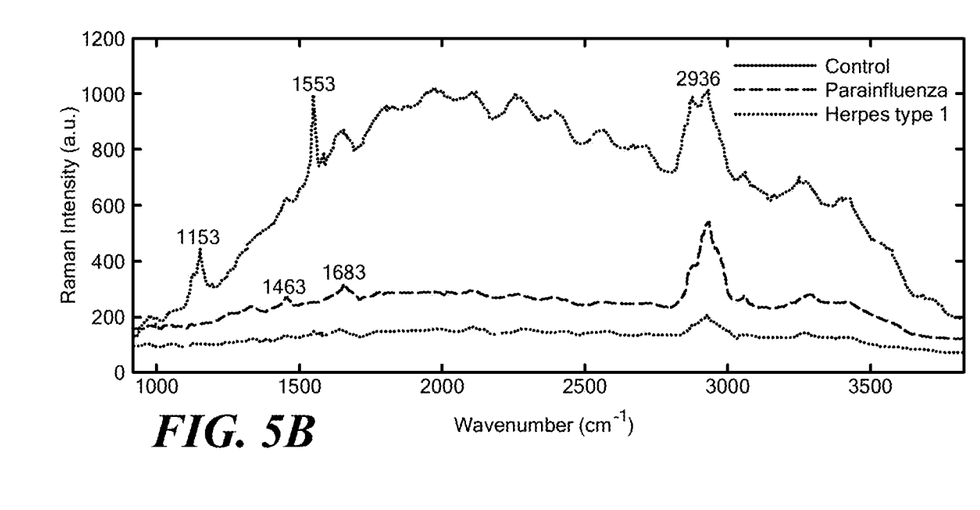
FIG. 5B shows spectra from two different viruses and a control spectrum.
Figure 5C:
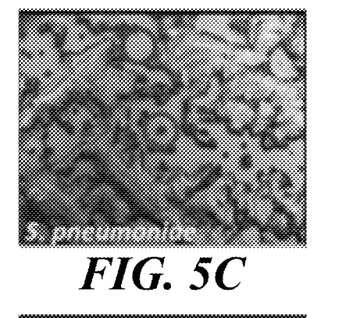
FIGS. 5C, 5D and 5E are bright field microscopic images of the respective samples where plotted spectra of FIGS. 5A and 5B were obtained.
Figure 5D:
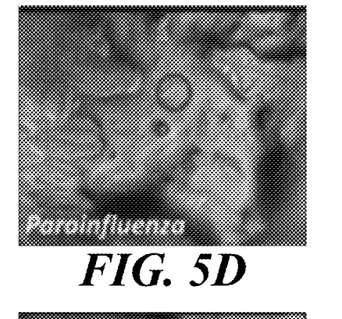
Figure 5E:
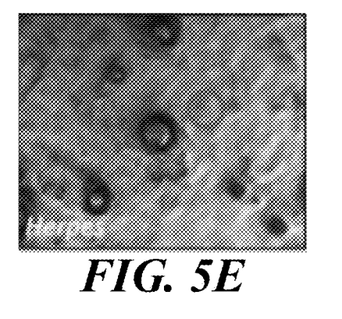

By way of example, FIG. 5A shows a Raman spectrum of the bacterial strain of *S. pneumoniae* (upper plot) relative to a control spectrum of desiccated crystallized phosphate-buffered saline (PBS) solution (lower plot). The Raman spectrum was obtained using a confocal Raman microscope system. FIG. 5B shows spectra from two different viruses (bovine parainfluenza virus type 3 and bovine herpes virus type 1) are shown in the lower plot, along with a control spectrum taken from a culture of only the host cells (Madin Darby bovine kidney cells). FIGS. 5C-5E are bright field microscopic images of the respective samples of FIGS. 5A and 5B, with circles indicating the approximate locations were the respective Raman spectra were obtained. FIGS. 5A-5B show differentiation in Raman spectra between bacterial and viral culture samples, as well as differentiation between two different viruses. Four vibrational peaks (1338 $cm^{-1}$, 1451 $cm^{-1}$, 1670 $cm^{-1}$, and 2935 $cm^{-1}$) identified in the spectrum of *S. pneumoniae* (FIG. 5A) correspond to those identified by Hartz et al., "*Direct analysis of clinical relevant single bacterial cells from cerebrospinal fluid during bacterial meningitis by means of micro-Raman spectroscopy,*" *J. Biophoton.*, vol. 2, pp. 70-80 (2009).

Other references that may be consulted for Raman spectra that distinguish among different types of bacterial, viral and fungal conditions are listed here:

Naumann, "*Infrared and NIR Raman Spectroscopy in Medical Microbiology,*" *Proc. SPIE* 3257, *Infrared Spectroscopy: New Tool in Medicine*, 245, (1998).

Krafft et al., "*Raman and CARS microspectroscopy of cells and tissues,*" *Analyst*, vol. 134, pp. 1046-57 (2009).

Zhu et al., "*Raman spectroscopic measurement of relative concentrations in mixtures of oral bacteria,*" *Appl Spectrosc.*, vol. 61, pp. 1233-37 (2007).

McEwen et al., "*Probing Nanostructures of Bacterial Extracellular Polymeric Substances (EPS) versus Culture Time by Raman Microspectroscopic and Atomic Force Microscopy,*" *Biopolymers*, vol. 93, pp. 171-77 (2010)

All of the foregoing references, as well as references cited therein, are incorporated herein by reference.

In accordance with certain embodiments of the present invention, aspects of quantitative otoscopic spectroscopy described herein may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

We claim:

1. A method for characterizing at least one of a middle ear fluid, a middle ear effusion, and a biofilm adjacent to a tympanic membrane of a person, the method comprising:
  a. illuminating a vicinity of the tympanic membrane with a broadband optical beam;
  b. interfering light scattered by the vicinity of the tympanic membrane with a reference beam derived from the broadband optical beam to generate an interferometric signal;
  c. illuminating the vicinity of the tympanic membrane with a monochromatic excitation beam, wherein the interferometric signal determines a focal region of the monochromatic excitation beam;
  d. coupling spontaneous Raman-scattered light from the vicinity of the tympanic membrane to a spectrometer;
  e. dispersing the spontaneous Raman-scattered light to obtain a Raman spectrum characterizing the spontaneous Raman-scattered light;
  f. ascertaining a first specified characteristic of any material adjacent to the tympanic membrane on the basis of the interferometric signal; and
  g. ascertaining a second specified characteristic of any material adjacent to the tympanic membrane on the basis of the Raman spectrum.

2. The method in accordance with claim 1, wherein the first specified characteristic is a measure of geometrical thickness of the tympanic membrane and any attached biofilm.

3. The method in accordance with claim 1, wherein the first specified characteristic is a measure of at least one of viscosity and turbidity.

4. The method in accordance with claim 1, wherein the first specified characteristic is an image.

5. The method in accordance with claim 1, wherein the material adjacent to the tympanic membrane of the person is at least one of a biofilm and effusion material.

6. The method in accordance with claim 1, wherein the second specified characteristic is at least one of a bacterial type, viral type and fungal type.

7. The method in accordance with claim 1, wherein the second specified characteristic is an identification of an extracellular polymeric substance.

* * * * *